United States Patent [19]

Landsiedel et al.

[11] Patent Number: 4,514,225

[45] Date of Patent: Apr. 30, 1985

[54] TRIORGANOTIN ACETYLSALICYLATES AND BIOCIDES CONTAINING THE SAME

[75] Inventors: Horst Landsiedel, Froendenberg; Hans Plum, Hamm, both of Fed. Rep. of Germany

[73] Assignee: Schering Aktiengesellschaft, Berlin and Bergkamen, Fed. Rep. of Germany

[21] Appl. No.: 581,652

[22] Filed: Feb. 21, 1984

[30] Foreign Application Priority Data

Feb. 22, 1983 [DE] Fed. Rep. of Germany ....... 3306036

[51] Int. Cl.³ .................................................. C09D 5/14
[52] U.S. Cl. .............................. 106/15.05; 260/429.7; 514/493
[58] Field of Search ................... 106/15.05; 260/429.7; 424/288

[56] References Cited

U.S. PATENT DOCUMENTS 3,288,669 11/1966 Hechenbleikner ............... 260/429.7
3,534,077 10/1970 Lombardo .......................... 424/288

*Primary Examiner*—Lorenzo B. Hayes
*Attorney, Agent, or Firm*—Francis W. Lemon

[57] ABSTRACT

What are disclosed are methods for rendering a substrate such as wood biocidal by treating the substrate with a biocidal triorganotin compound of the formula

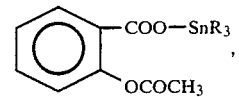

wherein R is cyclohexyl, phenyl, or alkyl having from 3 to 8 carbon atoms.

13 Claims, No Drawings

TRIORGANOTIN ACETYLSALICYLATES AND BIOCIDES CONTAINING THE SAME

The present invention relates to methods for rendering a substrate such as wood biocidal by treating the substrate with a triorganotin compound of the formula $$\text{C}_6\text{H}_4(\text{COO–SnR}_3)(\text{OCOCH}_3)$$

wherein R is cyclohexyl, phenyl, or alkyl having from 3 to 8 carbon atoms. More in particular, the invention relates to the use of such biocides against bacteria, fungi, algae, and marine growth organisms, or in wood preservation for the control of wood-attacking fungi.

Triorganotin compounds are known to possess good biocidal activity which extends to bacteria, fungi, algae, and certain marine organisms, for example, balanids and tube worms.

The biocidal activity of triorganotin compounds of the $R_3SnX$ type, wherein R represents alkyl, cyclohexyl, phenyl group and X an anionic group, is determined primarily by the chain length of the hydrocarbon groups linked to the tin. Optimum activity is obtained when the total number of the carbon atoms linked to the tin in alkyltin compounds ranges from 9 to 12, in other words, with tripropyltin and tributyltin compounds. (See Bokranz/Plum, Fortschritte der chemischen Forschung, vol. 16, Nos. 3–4, p. 377.) Triphenyltin compounds exhibit comparable biocidal activity.

The anionic group X usually has no effect on the biocidal activity of triorganotin compounds. (See International Tin Research Institute, Publication NO. 599, 1979; Bokranz/Plum, loc. cit.) The activity is determined by the trialkyltin content.

Thus, tributyl esters of long-chain acids, for example, tributyltin naphthenate or tributyltin linoleate, which contain only about half as much tin as tributyltin oxide, must be used in amounts about twice as large as TBTO to obtain the same biocidal activity.

The anionic group X influences the physical properties of triorganotin compounds. For example, tributyltin oxide and tributyltin chloride are low-viscosity liquids, tributyltin abietate and tributyltin phosphate are medium to high-viscosity liquids, and tributyltin fluoride is a solid. The triorganotin compound most widely used for the protection of materials is tri-n-butyltin oxide. When the oxygen in that compound is replaced by other anionic groups (for example, acid groups of organic or inorganic acids), products of lower water solubility and lower volatility are generally obtained.

It has now been found that triorganotin acetylsalicylates of the formula $$\text{C}_6\text{H}_4(\text{COO–SnR}_3)(\text{OCOCH}_3)$$

wherein R is cyclohexyl, phenyl, or alkyl having from 3 to 8 carbon atoms, and more particularly 4 carbon atoms, possess a significantly higher biocidal activity, on the basis of the triorganotin content, than do other triorganotin compounds and, thus, are particularly useful for the treatment of substrates to render the substrate biocidal. A preferred biocide is one which contains tri-n-butyltin acetylsalicylate as an active ingredient.

These compounds are new and, with the exception of tri-n-butyltin acetylsalicylate (see R. A. Cummins et al., "The Infrared Spectra of Organotin Compounds", Australia Commonwealth Dept. Supply Defense Std. Lab. Report 266, 106 pp., 1963), so far have not been described in the literature.

A test was run to determine the biocidal activity of triorganotin acetylsalicylates. Filter-paper disks 5.5 cm in diameter were impregnated with graded concentrations of the active substance in ethanol, air-dried, placed on nutrient agar in Petri dishes, inoculated with a bacterial suspension and a spore suspension of test fungi, respectively, and incubated for 2 days at 37° C. (bacteria) and for 3 weeks at 30° C. (fungi). Then the zones of inhibition around the specimens were measured in millimeters. Tri-n-butyltin oxide (TBTO) and tri-n-butyltin benzoate (TBTB) as well as triorganotin chlorides were used for comparison. (See following Table I.)

The biocidal activity of tri-n-butyltin acetylsalicylate (TBTAS) with a tributyltin content of about 61 percent was found to be as good as that of tri-n-butyltin oxide with a tributyltin content of about 95 percent.

Despite its lower tributyltin content, TBTAS has a significantly higher biocidal activity than TBTB.

The tricyclohexyltin, triphenyltin, tripropyltin and trioctyltin acetalsalicylates in some cases also exhibit better biocidal activity, with lower triorganotin contents, than do the corresponding chlorides.

TABLE I

OVERLAY TEST
Zones of inhibition around the specimens in mm

| Active substance | Content of impregnating solution (%) | Bacteria | | | Fungi | | | | | |
|---|---|---|---|---|---|---|---|---|---|---|
| | | Bac. mes. | Bac. subt. | Prot. vulg. | Pull. pull. | Asp. vers. | Clad. herb. | Con. put. | Chaet. glob. | Trich. vir. |
| TBTO | 2 | 10–12 | 12–15 | 5–6 | 3–5 | 12–15 | 6–8 | >15 | 12–15 | 4–5 |
| (Tributylin content, | 1 | 8–10 | 12–15 | 4–5 | 2–3 | 10–12 | 6–8 | 10–12 | 10–12 | 3–4 |
| approx. 95%) | 0.5 | 6–8 | 10–12 | 3–4 | 0–1 | 8–10 | 2–3 | 6–8 | 6–8 | 2–3 |
| | 0.25 | 6–8 | 10–12 | 2–3 | 0+ | 8–10 | 0 | 3–4 | 3–4 | 0 |
| TBTB | 2 | 8–10 | 8–10 | 2–3 | 2–3 | 8–10 | 3–4 | 8–10 | 8–10 | 1–2 |
| (Tributyltin content, | 1 | 6–8 | 8–10 | 1–2 | 0–1 | 6–8 | 2–3 | 6–8 | 7–9 | 0–1 |
| approx. 70%) | 0.5 | 3–4 | 6–8 | 1–2 | 0–1 | 5–7 | 1–2 | 3–4 | 3–4 | 0 |
| | 0.25 | 2–3 | 4–6 | 0 | 0++ | 3–4 | 0+ | 0–1 | 1–2 | 0++ |
| TBTAS | 2 | 12–15 | 12–15 | 5–7 | 2–3 | 10–12 | 6–8 | 12–15 | 12–15 | 4–5 |
| (Tributyltin content, | 1 | 10–12 | 12–15 | 5–7 | 1–2 | 10–12 | 5–7 | 12–15 | 12–15 | 4–5 |
| approx. 61%) | 0.5 | 10–12 | 10–12 | 4–6 | 0–1 | 10–12 | 3–4 | 6–8 | 8–10 | 2–3 |
| | 0.25 | 6–8 | 10–12 | 2–3 | 0+ | 8–10 | 0 | 3–4 | 5–7 | 0 |
| Tricyclohexyltin | 2 | 6–8 | 6–8 | 1–2 | 2–3 | 6–8 | 1–2 | 8–10 | 4–5 | 1–2 |

TABLE I-continued

OVERLAY TEST
Zones of inhibition around the specimens in mm

| Active substance | Content of impregnating solution (%) | Bacteria | | | Fungi | | | | | |
|---|---|---|---|---|---|---|---|---|---|---|
| | | Bac. mes. | Bac. subt. | Prot. vulg. | Pull. pull. | Asp. vers. | Clad. herb. | Con. put. | Chaet. glob. | Trich. vir. |
| chloride (Triorganotin content: 91%) | 1 | 4–6 | 4–5 | 0–1 | 1–2 | 4–6 | 0–1 | 4–6 | 3–4 | 0–1 |
| Tricyclohexyltin acetylsalicylate (Triorganotin content: 67%) | 2 | 5–7 | 8–10 | 2–3 | 3–4 | 8–10 | 3–4 | 12–15 | 8–10 | 3–4 |
| | 1 | 5–7 | 4–6 | 1–2 | 2–3 | 8–10 | 1–2 | 10–12 | 0–8 | 2–3 |
| Triphenyltin chloride (Triorganotin content: 91%) | 2 | 6–8 | 6–8 | 1–2 | 1–2 | 6–8 | 1–2 | 6–8 | 5–6 | 1–2 |
| | 1 | 3–4 | 6–8 | 0–1 | 1–2 | 3–4 | 0–1 | 6–8 | 4–5 | 1–2 |
| Triphenyltin acetylsalicylate (Triorganotin content: 66%) | 2 | 6–8 | 8–10 | 2–3 | 3–4 | 8–10 | 3–4 | 12–15 | 10–12 | 3–4 |
| | 1 | 4–6 | 6–8 | 2–3 | 1–2 | 4–5 | 3–4 | 12–15 | 8–10 | 2–3 |
| Triproplytin chloride (Triorganotin content: 87%) | 1 | 10–12 | 12–15 | 4–6 | 2–3 | 12–15 | 4–6 | 12–15 | 10–12 | 3–4 |
| | 0.5 | 6–8 | 10–12 | 4–6 | 2–3 | 8–10 | 4–6 | 8–10 | 10–12 | 2–3 |
| Tripropyltin acetylsalicylate (Triorganotin content: 58%) | 1 | 12–15 | 12–15 | 6–8 | 4–6 | 12–15 | 8–10 | >15 | >15 | 4–5 |
| | 0.5 | 10–12 | 12–15 | 4–6 | 4–5 | 12–15 | 6–8 | >15 | 12–15 | 4–5 |
| Trioctyltin chloride (Triorganotin content: 93%) | 4 | 3–4 | 4–5 | 1–2 | 0–1 | 4–5 | 0–1 | 3–4 | 4–6 | 0–1 |
| | 2 | 2–3 | 2–3 | 0 | 0–1 | 3–4 | 0–1 | 3–4 | 4–6 | 0–1 |
| Trioctyltin acetylsalicylate (Triorganotin content: 72%) | 4 | 3–4 | 4–6 | 1–2 | 1–2 | 6–8 | 3–4 | 4–5 | 4–5 | 1–2 |
| | 2 | 3–4 | 4–6 | 1–2 | 1–2 | 4–6 | 2–3 | 3–4 | 3–4 | 0–1 |
| Blank test | — | 0 | 0 | 0 | 0+++ | 0+++ | 0+++ | 0+++ | 0+++ | 0+++ |

\+ = light growth on specimen
++ = medium growth on specimen
+++ = marked growth on specimen The very good fungicidal activity of the tri-n-butyltin compounds used in accordance with the invention as active biocidal substances is apparent also from a comparison of their toxic limits with those of tri-n-butyltin oxide. These values were determined on pinewood (from *Pinus sylvestris L.*) against the test fungus *Coniophora cerebella* (BAM Ebw 15):

| | Toxic limits in kg/cm³ wood |
|---|---|
| Tri-n-butyltin oxide | 0.45–0.65 |
| Tri-n-butyltin acetylsalicylate | 0.20–0.32 |

(The smaller value reported is that concentration at which attack of the substrate by the microorganism is still just hindered by the biocide: the larger value is the concentration of biocide at which attack by the substrate is fully inhibited.)

The compounds in accordance with the invention can be prepared by reacting acetylsalicylic acid with triorganotin oxides or hydroxides, or with triorganotin chlorides suitably in the presence of an alkaline hydroxide.

The biocides comprising triorganotin acetylsalicylates in accordance with the invention are exceptionally well suited for the protection of materials, and especially for the preservation of wood, in that they prevent decay or attach by microorganisms. They can be used conventionally as solutions, emulsions, or dispersions in water or organic solvents, with or without binders, and optionally with the addition of wetting agents, adhesion promoters, emulsifiers and dispersants, to protect textiles, building materials, and plastics, for example.

For the preservation of wood, the compounds may be used as solutions or emulsions, optionally with the addition of binders and of dyes and auxiliary substances, and are applied to the wood by spread coating, spraying, or dipping, for example.

To broaden their biocidal spectrum, the biocides of the invention may be combined with other active biocidal substances, such as chlorinated phenols, salts of N'-hydroxy-N-cyclohexyldiazenium oxide, N-cyclohexyl-N-methoxy-2,5-dimethylfuran-3-carboxylamide, N,N-dimethyl-N'-phenyl-N'-(fluordichlormethylthio)sulfamide (dichlofluanide), and N-(fluordichlormethylthio)-4-cyclohexane-1,2-dicarboximide (fluorfolpet).

For wood preservation, combinations with active insecticidal substances, such as carbamates, phosphoric esters, chlorinated hydrocarbons, and pyrethroids, may be used, if desired.

With appropriate emulsifiers such as alkylarylpolyglycol ethers or carboxylic acid polyglycol esters, they can be used to formulate aqueous preparations (solutions or suspensions) which when diluted with water give clear or opalescent stable mixtures. These preparations are suited for the preservation of freshly felled timber, for the biocidal treatment of aqueous coating systems, papers, paperboards, textiles, and building materials, as well as to protect water baths from undesired microorganisms in recirculating cooling waters, drilling and cutting oils, and water used in paper manufacture.

The water dilutable preparations may contain the compounds of the invention in concentrations ranging from 5 to 35 weight percent. For use in treating substrates, these aqueous concentrates are diluted so that the concentration of active agent is from 0.1 to 5 percent, preferably from 0.3 to 3 percent. Similar concentrations of the active compounds can be used in organic solutions or other formulations.

When used in cooling water systems, paper manufacture, and the like, the compounds may be used in concentrations as low as 0.001 percent by weight, e.g. from 0.001 to 3 percent.

A better understanding of the present invention and of its many advantages will be had by referring to the following Examples, given by way of illustration.

EXAMPLE 1

Tri-n-butyltin acetylsalicylate was prepared as follows.

1 mole (180.16 g) of acetylsalicylic acid was heated with 0.5 mole (298.04 g) of tri-n-butyltin oxide to about 110° C. with stirring and maintained at that temperature for 1 hour. The reaction water formed was then eliminated by applying a low vacuum of about 0.1 bar. The resulting product was a liquid of pale yellow color whose characteristics were as follows:

Tin content: 25.4 wt. % (theory, 25.3 wt. %)
Viscosity: 145 Pa.sec at 20° C.
Density: 1.235 at 23° C.

The product was soluble in ethanol, xylene, hexane, mineral spirits, butyl diglycol, acetone, and chlorinated hydrocarbons.

EXAMPLE 2

Triphenyltin acetylsalicylate was prepared as follows.

1 mole (180.16 g) of acetylsalicylic acid was refluxed with 0.5 mole (358 g) of triphenyltin oxide and 1000 ml of xylene with stirring. The reaction water formed was eliminated within about 1 hour by azeotropic distillation through a xylene bridge. The xylene was then separated in a rotary evaporator. A solid resinous product was obtained whose characteristics were as follows:

Tin content: 22.0 wt. % (theory, 22.4 wt. %).
Melting point: 43° C.

The product was soluble in acetone, xylene, and methylene chloride.

EXAMPLE 3

Tricyclohexyltin acetylsalicylate was prepared as follows.

1 mole (180.16 g) of acetylsalicylic acid was refluxed with 1 mole (365.16 g) of tricyclohexyltin hydroxide and 1000 ml of xylene with stirring. The reaction water formed (1 mole) was eliminated within 1 hour by azeotropic distillation through a xylene bridge. The xylene was then separated in a rotary evaporator. A semisolid viscous product having a tin content of 21.1 wt. % (theory, 21.7 wt. %) was so obtained.

The product was soluble in ethanol, methylene chloride, xylene, and mineral spirits.

EXAMPLE 4

Trioctyltin acetylsalicylate was prepared as follows.

1 mole (180.16 g) of acetylsalicylic acid was heated with 1 mole (493.82 g) of trioctyltin chloride to about 50° C. with stirring. Then 1 mole (40 g) of NaOH in solid form was added in portions and the temperature was raised to 100° C. and maintained at that level for 1½ hours. The precipitated NaCl was then drawn off by means of a nutsch filter. The filtrate was washed in the separatory funnel four times with 500 ml portions of water and then dried over anhydrous sodium sulfate. A liquid product was obtained which had the following characteristics:

Tin content: 19.2 wt. % (theory, 18.6 wt. %)
Viscosity: 580 mPa/sec at 20° C.

The product was soluble in ethanol, xylene, mineral spirits, butyl diglycol, hexane, and chlorinated hydrocarbons.

EXAMPLE 5

Tri-n-propyltin acetylsalicylate was prepared as follows.

2 moles (360.32 g) of acetylsalicylic acid were heated with 1 mole (511.92 g) of tri-n-propyltin oxide to about 110° C. with stirring and held at that temperature for 1 hour. The reaction water formed was then eliminated by applying a low vacuum of about 0.1 bar. The product obtained was a liquid of pale yellow color with a tin content of 28.3 wt. % (theory, 27.8 wt. %).

The product was soluble in ethanol, xylene, mineral spirits, and chlorinated hydrocarbons.

EXAMPLE 6

An amount of 200 g/m² of tri-n-butyltin acetylsalicylate, as a 1.5% solution in mineral spirits (about 250 ml/m²), was applied by painting onto pine blocks of the dimensions 5×2.5×1.5 cm, the front surfaces of which were sealed. After drying at room temperature (2–3 weeks), the blocks were sterilized and are exposed to the attack of the wood-destroying fungus *Coniophora puteana* (according to the test method DIN 56176). After twelve weeks, the loss of weight brought about by the attack of the fungus was determined in comparison with the weight of untreated wood samples.

| Sample | Loss of Weight (%) |
| --- | --- |
| Untreated wood blocks | (median) 33.9 |
|  | 37.1–31.3 |
| Treated test samples | (median) 1.9 |
|  | 2.6–1.6 |

Thus, painting with a 1.5% solution of tri-n-butyltin acetylsalicylate in mineral spirits to apply an amount of 200 g/m² of the active agent provides good protection against *Coniophora puteana*.

EXAMPLE 7

A woven cloth (surface weight 600 g/m²) was saturated with different concentrations of triphenyltin acetylsalicylate in ethanol. After drying at room temperature (1 week) the test pieces were buried in the open in garden soil. After six weeks, the test samples were taken out, rinsed, dried, and visually judged for decomposition.

| Sample No. | Active agent in saturating solution (%) | Valuation |
| --- | --- | --- |
| 1 | 0 | strong discoloration and partial destruction |
| 2 | 0.1 | strong discoloration, individual portions of the fabric surface destroyed |
| 3 | 0.2 | clearly detectable discoloration, very little destruction |
| 4 | 0.4 | individual points discolored, no recognizable destruction |
| 5 | 0.7 | individual points discolored, no |

| Sample No. | Active agent in saturating solution (%) | Valuation |
| --- | --- | --- |
| | | detectable destruction |
| 6 | 1.0 | no discoloration and no destruction |

Cotton fabric can effectively be protected against rotting by saturation in a 0.5% by weight solution of triphenyltin acetylsalicylate.

EXAMPLE 8

Small blocks of pine wood having the dimensions 5×2.5×1.5 cm were dried for 24 hours at 103° C. and weighed. Sets of five blocks each were saturated with varying concentrations of tricyclohexyltin acetylsalicylate in chloroform under vacuum (10 mbar). After drying at room temperature, the toxic limits for *Poria monticula* were determined according to DIN 56176, i.e. those concentrations were determined at which, on the one hand, an attack on the wood just still occurs (loss of weight greater than 3%) and, on the other hand, no attack occurs (loss of weight less than 3%).

| Samples | Content of the saturating solution (%) | kg of Fungicide/ m³ wood | Loss of weight (%) |
| --- | --- | --- | --- |
| 1 | 0 | 0 | (median) 26.4 27.1–25.6 |
| 2 | 0.0063 | 0.068 | (median) 27.2 27.9–24.8 |
| 3 | 0.010 | 0.095 | (median) 11.7 12.4–10.1 |
| 4 | 0.016 | 0.22 | (median) 4.0 2.9–4.5 |
| 5 | 0.025 | 0.34 | (median) 2.3 1.1–3.0 |
| 6 | 0.040 | 0.48 | (median) 2.2 1.0–2.4 |
| 7 | 0.063 | 0.61 | (median) 2.3 1.2–2.6 |

The toxic limits of tricyclohexyltin acetylsalicylate for *Poria monticula* are 0.22–0.34 kg/m³ of wood.

EXAMPLE 9

Using the method of Example 6, the loss of weight in pine wood test blocks treated by painting with 1.5% and 2.5% solutions of trioctyltin acetylsalicylate in mineral spirits, with the addition of 5% by weight of a linseed oil alkyd resin of high oil length (about 68–80 percent), was determined against *Lentinus lepideus*.

| Sample | Loss in weight (%) |
| --- | --- |
| Untreated control blocks | (median) 31.2 33.0–29.9 |
| Test samples, painted with 1.5% of active agent | (median) 5.1 6.3–4.7 |
| Test samples, painted with 2.5% of active agent | (median) 2.5 2.0–2.8 |

Good protection against *Lentinus lepideus* is afforded by the use of a 2.5% by weight solution of trioctyltin acetylsalicylate in mineral spirits when applied in an amount of 200 g/m³.

EXAMPLE 10

An antifouling paint was formulated from the following components:
  13.5 parts by weight of chlorinated rubber, ("Pergut S 20"),
  8.5 parts by weight of chlorinated paraffin ("Witachlor 544"),
  8 parts by weight of tri-n-propyltinacetylsalicylate,
  30 parts by weight of titanium dioxide, and
  40 parts by weight of xylene.

The components were homogenized by brief stirring and passed twice through a three roller rolling mill. The antifouling paint so obtained was painted onto resin sheets. After drying, the sheets were exposed in both the North Sea and in the Baltic Sea. The time of observation extended over about twelve months, during which no growth appeared on the test sheets.

EXAMPLE 11

A water dilutable formulation was prepared from the following ingredients:
  24 parts by weight of tri-n-butyltinacetylsalicylate,
  56 parts by weight of a non-ionic emulsifier (a mixture of carboxylic acid polyglycol esters), and
  20 parts by weight of water.

The components were combined in the aforementioned order with stirring at room temperature. After about five minutes of stirring, a clear mixture was obtained which could be diluted in water in every proportion.

Different concentrations of the aforementioned formulation were stirred into a pigmented dispersion paint comprising an acrylate/styrene copolymer having a solids content of 52% by weight. Thin synthetic resin sheets (4×4 cm) were painted with the fortified paints and, after drying, were placed on Petri dishes containing agar which had been sprayed with suspensions of spores of different test fungi. After an incubation time of four weeks at 30° C., the zone of inhibition of the fungal growth on the agar samples was determined.

| Amount of formulation added (wt. %) | ZONES OF INHIBITION (mm) | | | | |
| --- | --- | --- | --- | --- | --- |
| | *Pullularia pullalans* | *Chadosporum herbarum* | *Scherophoma pithyophila* | *Aspergillus versicolor* | *Paecillomyces varioti* |
| 0 | 0+++ | 0+++ | 0+++ | 0+++ | 0+++ |
| 0.5 | 0++ | 0+ | 0 | 0+ | 0 |
| 1.0 | 0+ | 1–2 | 2–3 | 2–3 | 3–4 |
| 2.0 | 1–2 | 4–5 | 4–5 | 6–8 | 8–10 |

-continued

| Amount of formulation added (wt. %) | ZONES OF INHIBITION (mm) | | | | |
|---|---|---|---|---|---|
| | Pullularia pullalans | Chadosporum herbarum | Scherophoma pithyophila | Aspergillus versicolor | Paecillomyces varioti |
| 3.0 | 5–6 | 8–10 | 12–15 | 10–12 | 12–15 |

+ = light growth of the sample
++ = medium growth of the sample
+++ = strong growth of the sample A dispersion paint comprising an acrylate/styrene copolymer can be adequately protected against the growth of blue fungi and mold fungi by the addition thereto of 1.5–2% by weight of a concentrated water dilutable formulation of tri-n-butyltinacetylsalicylate having a content of active agent of 24%.

EXAMPLE 12

A water dilutable formulation is prepared from the following components:
15 parts by weight of tricyclohexyltinacetylsalicylate (from Example 3),
25 parts by weight of a non-ionic emulsifier (alkylaryl polyglycolether),
60 parts by weight of water, and
0.001 part by weight of a silicon antifoaming agent.
The components were combined in the aforementioned order with stirring at room temperature. After about 5 minutes of stirring time, a clear mixture was obtained which could be diluted with water in all proportions.

The cooling water system of a production plant was treated with this product. The volume of cooling water was 1,400 m$^3$. The aforementioned formulation was in each case added to the water and concentration of 20 parts per million on each of five successive days.

The water showed the following germ counts:

| Day of treatment | | Germ/ml |
|---|---|---|
| First Day before addition | | 59,000 |
| | First addition | |
| First Day: | 4 hours after the first addition | 21,000 |
| | 12 hours after the first addition | 37,000 |
| | 24 hours after the first addition | 48,000 |
| | Second addition | |
| Second Day: | 4 hours after the second addition | 18,000 |
| | 12 hours after the second addition | 33,000 |
| | 24 hours after the second addition | 46,000 |
| | Third addition | |
| Third Day: | 4 hours after the third addition | 11,000 |
| | 12 hours after the third addition | 12,000 |
| | 24 hours after the third addition | 27,000 |
| | Fourth addition | |
| Fourth Day: | 4 hours after the fourth addition | 14,000 |
| | 12 hours after the fourth addition | 27,000 |
| | 24 hours after the fourth addition | 40,000 |
| | Fifth addition | |
| Fifth Day: | 4 hours after the fifth addition | 18,000 |
| | 12 hours after the fifth addition | 13,000 |
| | 24 hours after the fifth addition | 21,000 |
| | 48 hours after the fifth addition | 32,000 |
| | 72 hours after the fifth addition | 55,000 |

The germ count of a plant cooling water system can be kept under the conventional limit of 50,000/ml by a daily single dosing of 20 parts per million (about 3 parts per million of active agent) of the aforementioned formulation.

What is claimed is:

1. A method for controlling the growth of bacteria, fungi, algae marine organisms on or in a substrate, which method comprises adding or applying to said substrate a compound of the formula

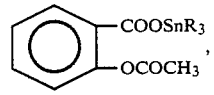

wherein R is cyclohexyl, phenyl, or alkyl having from 3 to 8 carbon atoms.

2. The method of claim 1 wherein said compound is applied to said substrate as a solution or suspension.

3. The method of claim 1 wherein said substrate is wood.

4. The method of claim 2 wherein said compound is applied by coating, spraying, or dipping said substrate with or in said solution or suspension.

5. The method of claim 1 wherein said compound is tri-n-butyltin acetylsalicylate.

6. The method of claim 1 wherein said substrate is water.

7. The method of claim 1 wherein said substrate is fabric.

8. The method of claim 1 wherein said substrate is a coating formulation.

9. The method of claim 8 wherein said coating formulation is an antifouling paint.

10. A compound of the formula

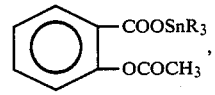

wherein R is phenyl or cyclohexyl.

11. A biocidal formulation comprising a solution or suspension of a compound of claim 10.

12. A concentrated formulation of claim 11 wherein said compound is present in an amount from 5 to 35 percent by weight.

13. A dilute formulation of claim 11 wherein said compound is present in an amount from 0.3 to 3 percent by weight.

* * * * *